United States Patent [19]

Sanderson et al.

[11] Patent Number: 5,097,085
[45] Date of Patent: Mar. 17, 1992

[54] PROCESS FOR OLIGOMERIZING OLEFINS USING PHOSPHOROUS-CONTAINING ACID ON MONTMORILLONITE CLAY

[75] Inventors: John R. Sanderson, Leander; John F. Knifton, Austin, both of Tex.

[73] Assignee: Texaco Chemical Company, White Plains, N.Y.

[21] Appl. No.: 551,969

[22] Filed: Jul. 12, 1990

[51] Int. Cl.$^5$ .............................................. C07C 2/74
[52] U.S. Cl. ..................................... 585/255; 585/527
[58] Field of Search ............................... 585/255, 527

[56] References Cited

U.S. PATENT DOCUMENTS

| | | | |
|---|---|---|---|
| 2,586,852 | 2/1952 | Morrell | 502/81 |
| 2,713,560 | 7/1955 | Morrell | 502/81 |
| 2,732,408 | 1/1956 | Foote | 568/791 |
| 2,951,087 | 8/1960 | Hauser et al. | 502/62 |
| 3,412,039 | 11/1968 | Miller | 502/81 |
| 3,432,571 | 3/1969 | Noddings et al. | 585/300 |
| 3,459,815 | 8/1969 | Noddings et al. | 568/896 |
| 3,673,111 | 6/1972 | Hoverth et al. | 502/213 |
| 3,845,150 | 10/1974 | Yan et al. | 208/135 |
| 3,849,507 | 11/1974 | Zuech | 585/455 |
| 3,959,399 | /1976 | Bridwell et al. | 585/458 |
| 4,153,638 | 5/1979 | Bercik et al. | 585/526 |
| 4,263,465 | 4/1981 | Sheng et al. | 585/255 |
| 4,299,730 | 11/1981 | Sommer et al. | 502/63 |
| 4,351,980 | 9/1982 | Reusser et al. | 585/820 |
| 4,380,509 | 4/1983 | Sommer et al. | 502/439 |
| 4,456,779 | 6/1984 | Owen et al. | 585/415 |
| 4,480,142 | 10/1984 | Cobb | 585/465 |
| 4,482,772 | 11/1984 | Tabak | 585/255 |
| 4,531,014 | 7/1985 | Gregory et al. | 585/415 |
| 4,604,491 | 8/1986 | Dressler et al. | 585/26 |
| 4,675,463 | 6/1987 | Glivicly et al. | 585/514 |
| 4,808,559 | 2/1989 | Sommer et al. | 502/63 |
| 4,827,064 | 5/1989 | Wu | 585/10 |
| 4,879,425 | 11/1989 | Kukes et al. | 585/350 |
| 4,946,815 | 8/1990 | Chao et al. | 585/529 |

FOREIGN PATENT DOCUMENTS 0353813 2/1990 European Pat. Off. .

OTHER PUBLICATIONS

Kuliev et al., "Preparation of High-Viscosity Synthetic Lubricants Using an Aluminosilicate Catalyst", Institute of Petrochemical Processes of the Academy of Sciences of the Azerbaidzhan SSR, *Azerbaidzhanskue, Nytiano, Khozinstuo,* 1983, No. 4, pp. 40–43.

Chaudhuri and Sharma, "Some Novel Aspects of the Dimerization of L-Methylstyrene with Acidic Ion-Exchange Resins Clays, and other Acidic Materials as Catalysts", Ind. Eng. Res., vol. 28, pp. 1757–1763 (1989).

Purnell, "Catalysis by Ion-Exchanged Montmoullonites", *Catalysis Letters,* 5 (1990), pp. 203–210.

Figueras, "Pillared Clays as Catalysts", *Catal. Rev. Sci. Eng.,* 30(3), pp. 457–499 (1988).

Friedlander, "Organized Polymerization I. Olefins on a Clay Surface", *Journal of Polymer Science: Part C,* No. 4, pp. 1291–1301.

Friedlander et al., "Organized Polymerization III, Monomers Intercalated in Montmorillonite", *Polymer Letters,* vol. 2.

"Intercalated Catalysts and Pillared Clays", Process Evaluation/Research Planning Report, Chem. Systems; Catalysts: Selected Developments, 84-3, pp. 239–249 (Dec. 1985).

Bolan, "Synthetic Lubricant Base Stocks", Process Economics Program Report No. 125A by SRI International, Apr. 1989 and Supplement A, Sept. 1989.

"Synthetic Lubricants from Internal Olefins", Process Evaluation/Research Planning Report by Chem. Systems, 84-Q-1, pp. 17–45.

Adams, "Synthetic Organic Chemistry Using Pillared Cation-Exchanged and Acid-Treated Montmorillonite Catalysts—A Review", *Applied Clay Science,* 2 (1987), pp. 309–342.

Adams et al., "Clays as Selective Catalysts in Organic Synthesis", Journal of Inclusion Phenomena, vol. 5 (1987), pp. 663–674.

*Primary Examiner*—W. J. Shine
*Assistant Examiner*—E. D. Irzinski
*Attorney, Agent, or Firm*—Jack H. Park; Kenneth R. Priem; Russell R. Stolle

[57] ABSTRACT

An improved process is disclosed for preparing synthetic lubricant base stocks. Synthetic lubricant base stocks are prepared in good yield by oligomerizing linear olefins using montmorillonite clays which have a phosphorous-containing acid deposited thereon.

25 Claims, No Drawings

PROCESS FOR OLIGOMERIZING OLEFINS USING PHOSPHOROUS-CONTAINING ACID ON MONTMORILLONITE CLAY

CROSS-REFERENCE TO RELATED APPLICATIONS

This application is related to the following co-pending U.S. Pat. applications: Ser. No. 07/500,631, filed Mar. 28, 1990, which relates to the preparation of synthetic lubricant base stocks by oligomerizing linear olefins by means of certain acidic montmorillonite clays; Ser. No. 07/516,931, filed Apr. 30, 1990, which relates to the preparation of synthetic lubricant base stocks by oligomerizing certain mixtures of internal and alpha-olefins by means of certain acidic montmorillonite clays; Ser. No. 07/516,870, filed Apr. 30, 1990, which relates to synthetic lubricant base stocks made by oligomerizing linear olefins by means of certain aluminum nitrate-treated acidic montmorillonite clays; Ser. No. 07/522,941, filed May 14, 1990, which relates to the preparation of synthetic lubricant base stocks by co-oligomerizing propylene and long-chain alpha-olefins by means of certain acidic montmorillonite clay catalysts; Ser. No. 07/525,807, filed May 21, 1990, which concerns synthetic lubricant base stocks made by co-oligomerizing 1,3-di-isopropenyl benzene and long-chain alpha-olefins by means of certain acidic montmorillonite clay catalysts; Ser. No. 07/531,172, filed May 31, 1990, which concerns synthetic lubricant base stocks having an improved pour point; Ser. No. 07/534,080, filed June 6, 1990, which concerns synthetic lubricant base stocks having an improved viscosity; Ser. No. 07/536,906, filed June 12, 1990, which concerns synthetic lubricant base stocks made by co-reacting olefins and anisole or like compounds; and Ser. No. 07/545,260, filed June 28, 1990, which concerns mixtures of oligomers and certain alkylated aromatics as synthetic lubricant base stocks. The totality of each of these previously filed applications is incorporated herein by reference.

BACKGROUND OF THE INVENTION

1. Field of the Invention

The invention relates to the preparation of synthetic lubricant base stocks, and more particularly to synthetic lubricant base stocks made by oligomerizing linear olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40-43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2/g$ or greater. In addition to being excellent catalysts, these clays are non-hazardous and non-polluting.

With respect to the present invention, Applicants have discovered, surprisingly, that an even higher conversion of olefin to oligomer may be obtained by contacting the olefin with a catalyst prepared by depositing a phosphorous-containing acid on a substrate comprising montmorillonite clay. Moreover, the process of the present invention results in a higher percentage of trimer and higher oligomers, another desirable feature.

SUMMARY OF THE INVENTION

The invention relates to a process for the preparation of oligomers, comprising the following steps: (a) depositing a phosphorous-containing acid on a substrate comprising montmorillonite clay; and (b) contacting a linear olefin containing from 10 to 24 carbon atoms with the phosphorous-containing-acid treated clay of step (a).

DESCRIPTION OF THE PREFERRED EMBODIMENTS

Applicants discovered that synthetic lubricant base stocks may be prepared in good yield by oligomerizing long-chain olefins using certain acidic montmorillonite clay catalysts, as described in the co-pending applications cross-referenced above. Applicants have further discovered that an improvement in the conversion of olefin to oligomer and in the resulting dimer/trimer ratio may be obtained where these or other montmorillonite clays are treated with a phosphorous-containing acid prior to use as an oligomerization catalyst.

The olefin monomer feed stocks used in the present invention may be selected from compounds comprising (1) alpha-olefins having the formula $R''CH=CH_2$, where $R''$ is an alkyl radical of 8 to 22 carbon atoms, and (2) internal olefins having the formula $RCH=CHR'$, where R and R' are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 14 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes well-known to those skilled in the art and are commercially available.

The oligomerization reaction may be represented by the following general equation:

where n represents moles of monomer and m represents the number of carbon atoms in the monomer. Thus, the oligomerization of 1-decene may be represented as follows:

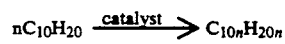

The reaction occurs sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The oligomers are prepared using certain silica-alumina clays, also called aluminosilicates, which have been treated with a phosphorous-containing acid. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

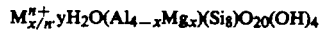

where M represents the interlamellar (balancing) cations, normally sodium or lithium; and x, y and n are integers.

As described in co-pending applications cross-referenced above, montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 M²/g or greater. Illustrative examples include Filtrol grade 24, having a moisture content of 12 wt. %, a residual acidity of 8.5 mg KOH/g, and a surface area of 425 M²/g; Filtrol grade 124, having a moisture content of 2 wt. %, a residual acidity of 7.0 mg KOH/g, and a surface area of 400 M²/g; Filtrol grade 13, having a moisture content of 16 wt. %, a residual acidity of 15 mg KOH/g, and a surface area of 300 M²/g; Filtrol grade 113, having a moisture content of 4 wt.%, a residual acidity of 10 mg KOH/g, and a surface area of 300 M²/g; and Filtrol grade 224, having virtually no moisture, and having a residual acidity of 3.0 mg KOH/g, and a surface area of 350 M²/g.

Applicants have now discovered that a higher conversion and an improved dimer/trimer ratio may be obtained by contacting the olefin feed with a catalyst prepared by depositing a phosphorous-containing acid on a substrate comprising a montmorillonite clay. The montmorillonite substrate may comprise a neutral to basic clay (i.e. having a pH of about 7 or greater), or one that has previously been acid treated as described above. Preferably, the clay has not been treated with an acid prior to its use as a substrate for the phosphorous-containing acid, and has a residual acidity of less than about 1 mg KOH/g. An especially preferred clay is Filtrol grade 2C, having a moisture content at 220° F. of 15 wt. % and a pH of 7.5. It is preferred that the phosphorous-containing acid to be deposited on the montmorillonite is hypophosphorous acid, hypophosphoric acid, orthophosphoric acid, metaphosphoric acid, or polyphosphoric acid. It is especially preferred that the phosphorous-containing acid be orthophosphoric acid.

In the present invention, the clay is treated with phosphorous-containing acid prior to running the oligomerization reaction. The clay should be added to a solution of about 2 to about 100 wt. %, preferably from about 60 to about 90 wt. %, phosphorous-containing acid in water. The ratio of clay to phosphorous-containing acid solution should be sufficient to provide a catalyst having a quantity of phosphorous deposited thereon ranging from about 0.1 to about 20 wt. %, preferably about 1 to about 5 wt. %. The clay should remain in the phosphorous-containing acid solution for a period of time and under agitation to the extent necessary to meet these requirements, and then filtered and dried. Optionally, the filtered phosphorous-containing-acid treated clay may be washed with distilled water and then dried, preferably under mild conditions.

Preferably, the phosphorous-containing-acid treated catalyst is heat treated before running the reaction. Applicants found that heat treatment of the catalyst prior to running the oligomerization reaction causes the catalyst to be more active and produce a higher olefin conversion. Additionally, clays heat treated in this manner are more stable, remaining active during the oligomerization reaction for a longer period of time. The clays may be heat treated at temperatures in the range of about 50° C. to 400° C., with or without the use of a vacuum. A more preferred temperature range is 50° C. to 300° C. Optionally, an inert gas may be used during heat treatment as well. Preferably, the clay should be heat treated under conditions and for a length of time which will reduce the water content of the clay to approximately 1 wt. % or less.

The oligomerization reaction may be carried out in either a stirred slurry reactor or in a fixed bed continuous flow reactor. The catalyst concentration should be sufficient to provide the desired catalytic effect. The temperatures at which the oligomerization may be performed ar between about 50° C. and 300° C., with the preferred range being about 150° C. to 180° C. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

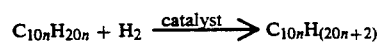

$$C_{10n}H_{20n} + H_2 \xrightarrow{\text{catalyst}} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal, or they may be formulated into a bulk metal catalyst. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer may be removed either prior to or after the hydrogenation step. Optionally, unreacted monomer may be stripped from the oligomers prior to hydrogenation and recycled to the catalyst bed for oligomerization. The removal or recycle of unreacted monomer or, if after hydrogenation, the removal of non-oligomerized alkane, should be conducted under mild conditions using vacuum distillation procedures known to those skilled in the art. Distillation at temperatures exceeding 250° C. may cause the oligomers to break down in some fashion and come off as volatiles. Preferably, therefore, the reboiler or pot temperature should be kept at or under about 225° C. when stripping out the monomer. Procedures known by those skilled in the art to be alternatives to vacuum distillation also may be employed to separate unreacted components from the oligomer.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention.

EXAMPLES

In the examples detailed below, the following procedures were used:

Preparation of $H_3PO_4$ on H/F Clay 2C

To 200 cc of Harshaw/Filtrol grade 2C powder was added 200 cc of orthophosphoric acid (85 wt. %). The mix was mechanically stirred for 1 hour at room temperature. The solids were filtered off and washed with distilled water until there was no phosphorous detected in the filtrate. The remaining solids were then dried under vacuum overnight at 40° C., followed by drying under vacuum for 4 hours at 150° C. Ninety grams of white powder were recovered. Analysis showed the presence of 2.2 wt. % phosphorous and 0.4 wt. % water, and a residual acidity of 9 mg KOH/g.

Oligomerization of Olefins

Olefin and catalyst were charged to a three-necked flask equipped with an overhead stirrer, thermometer, heating mantle, and a water-cooled condenser ($N_2$ purge). The mixture was vigorously stirred and heated to the desired temperature for the desired time. The mixture was then cooled to ambient temperature and filtered with suction. The liquid was analyzed by liquid chromatography. The results obtained with phosphoric acid treated montmorillonites are detailed in Table I. Comparative results are provided in Table II.

TABLE I

OLEFIN OLIGOMERIZATION WITH PHOSPHORIC ACID TREATED CLAYS

| Ex. No. | Olefin(s) (by carbon number) | Catalyst | Amount of Catalyst (wt. %) | Time/Temp. (Hr)/(°C.) | Olefin Con. (%) | Dimer/ Trimer+ Ratio |
|---|---|---|---|---|---|---|
| 1 | C-14A | $H_3PO_4$ on H/F Clay 2C | 10 | 5.0/160 | 80.8 | 0.87 |
| 2 | C-14A, 16A | $H_3PO_4$ on H/F Clay 2C | 10 | 5.0/160 | 78.4 | 1.23 |
| 3 | C-15I, 18I | $H_3PO_4$ on H/F Clay 2C | 10 | 5.0/160 | 61.4 | 3.15 |
| 4 | C-14A | $H_3PO_4$ on H/F Clay 2C | 10 | 5.0/160 | 80.2 | 1.18 |
| 5 | C-15I, 18I | $H_3PO_4$ on H/F Clay 2C | 10 | 5.0/160 | 60.2 | 3.46 |

Con. = Conversion; A = Alpha; I = Internal; and Trimer+ = Trimer + Tetramer + Pentamer, etc.

Hydrogenation of Oligomer

An autoclave was charged with oligomer prepared in Example No. 4 of Table I and finely powdered nickel-copper-chromia catalyst. The autoclave was flushed with hydrogen and then pressured to 1000 psig with hydrogen. The mixture was heated to 200° C. and stirred at this temperature for 4 hours. The mixture was then repressured with hydrogen to 2000 psig as needed. The mixture was then cooled to ambient temperature, the catalyst was filtered and the monomer was removed. The procedure was repeated for the oligomer prepared in Example 5. The following properties were obtained:

| Ex. No. | Percent Remaining by TGA (250° C.) | Viscosity (cSt at 210° F.) | Viscosity Index | Pour Point |
|---|---|---|---|---|
| 4 | 90.7 | 5.70 | 134 | −20° F. |
| 5 | 93.1 | 5.87 | 123 | −20° F. |

TGA = Thermogravimetric Analysis

TABLE II

OLEFIN OLIGOMERIZATION WITH PHOSPHORIC ACID TREATED CLAYS

| Ex. No. | Olefin (by carbon number) | Catalyst | Amount of Catalyst (Wt. %) | Time/Temp (Hr)/(°C.) | Olefin Con. (%) | Dimer/ Trimer+ Ratio |
|---|---|---|---|---|---|---|
| 6 | C-14A | Norton Phosphate Catalyst | 10 | 5.0/160 | ∼0 | — |
| 7 | C-14A | $H_3PO_4$ on Activated Bauxite | 10 | 4.0/180 | 10.3 | 3.44 |
| 8 | C-14A | $H_3PO_4$ on 3A Molecular Sieves | 10 | 4.0/180 | ∼0 | — |
| 9 | C-14A | $H_3PO_4$ on 4A Molecular Sieves | 10 | 4.0/180 | ∼0 | — |
| 10 | C-14A | $H_3PO_4$ on 5A Molecular Sieves | 10 | 4.0/180 | 4.75 | — |
| 11 | C-14A | $H_3PO_4$ on 13X Molecular Sieves | 10 | 4.0/180 | 2.75 | — |
| 12 | C-14A | $H_3PO_4$ on $SiO_2$ (VCI Polycatalyst) | 10 | 5.0/160 | 2.03 | — |
| 13 | C-14A | $H_3PO_4$ on $TiO_2$ | 10 | 5.0/160 | ∼0 | — |

Con. = Conversion; M = Monomer; D = Dimer; T+ = Trimer + Tetramer + Pentamer, etc; A = Alpha; I = Internal.

Molecular sieves are crystalline metal aluminosilicates having the following compositions: 3A = $0.6K_2O:0.4Na_2O:1Al_2O_3:2SiO_2$; 4A = $1Na_2O:1Al_2O_3:2SiO_2$; 5A = $0.8CaO:0.2Na_2O:1Al_2O_3:2SiO_2$; 13X = $1Na_2O:1Al_2O_3:2.8SiO_2$. Bauxite refers to rocks that contain significant quantities of aluminum hydroxide minerals, such as, for example, $Fe_2O_3.Al_2O_3$.

We claim:

1. A process for the preparation of oligomers, comprising the following steps: (a) depositing a phosphorous-containing acid on a substrate comprising montmorillonite clay; and (b) contacting a linear olefin containing from 10 to 24 carbon atoms with the phosphorous-containing-acid treated clay of step (a).

2. The process of claim 1, wherein the montmorillonite clay has a residual acidity of less than about 1 mg KOH/g prior to treatment with the phosphorous-containing acid.

3. The process of claim 1, wherein the montmorillonite clay has a pH of about 7 or greater prior to treatment with the phosphorous-containing acid.

4. The process of claim 1, wherein, prior to treatment with the phosphorous-containing acid, the moisture content of the clay is about 15 wt. % and the pH is about 7.5.

5. The process of claim 1, wherein the montmorillonite clay is an acidic calcium montmorillonite clay having, prior to treatment with the phosphorous-containing acid, a moisture content ranging up to about 20 wt. %, a residual acidity in the range of about 3 to about 30 mg KOH/g, and a surface area of about 300 $M^2/g$ or greater.

6. The process of claim 1, wherein the olefin contains from 14 to 16 carbon atoms.

7. The process of claim 1, wherein the phosphorous-containing acid is hypophosphorous acid, hypophosphoric acid, orthophosphoric acid, metaphosphoric acid, or polyphosphoric acid.

8. The process of claim 1, wherein the phosphorous-containing acid is orthophosphoric acid.

9. A process for the preparation of oligomers, comprising contacting a linear olefin containing from 10 to 24 carbon atoms with a phosphorous-containing-acid treated montmorillonite clay having a phosphorous content of up to about 5 wt. %.

10. The process of claim 9, wherein the montmorillonite clay has a residual acidity of less than about 1 mg KOH/g prior to treatment with the phosphorous-containing acid.

11. The process of claim 9, wherein the montmorillonite clay has a pH of about 7 or greater prior to treatment with the phosphorous-containing acid.

12. The process of claim 9, wherein, prior to treatment with the phosphorous-containing acid, the moisture content of the clay is about 15 wt. % and the pH is about 7.5.

13. The process of claim 9, wherein the montmorillonite clay is an acidic calcium montmorillonite clay having, prior to treatment with the phosphorous-containing acid, a moisture content ranging up to about 20 wt. %, a residual acidity in the range of about 3 to about 30 mg KOH/g, and a surface area of about 300 $M^2/g$ or greater.

14. The process of claim 9, wherein the olefin contains from 14 to 16 carbon atoms.

15. The process of claim 9, wherein the phosphorous-containing acid is hypophosphorous acid, hypophosphoric acid, orthophosphoric acid, metaphosphoric acid, or polyphosphoric acid.

16. The process of claim 9, wherein the phosphorous-containing acid is orthophosphoric acid.

17. The process of claim 9, wherein the phosphorous-containing-acid treated montmorillonite clay has a phosphorous content of about 1 to about 5 wt. %.

18. A process for the preparation of a synthetic lubricant base stock, comprising the following steps:
(a) depositing a phosphorous-containing acid on a substrate comprising montmorillonite clay; (b) contacting a linear olefin containing from 10 to 24 carbon atoms with the phosphorous-containing-acid treated clay of step (a); (c) separating out any remaining un-oligomerized olefin; and (d) hydrogenating the oligomer fraction resulting from step (c) to produce a synthetic lubricant component.

19. The process of claim 18, wherein the montmorillonite clay has a residual acidity of less than about 1 mg KOH/g prior to treatment with the phosphorous-containing acid.

20. The process of claim 18, wherein the montmorillonite clay has a pH of about 7 or greater prior to treatment with the phosphorous-containing acid.

21. The process of claim 18, wherein, prior to treatment with the phosphorous-containing acid, the moisture content of the clay is about 15 wt. % and the pH is about 7.5.

22. The process of claim 18, wherein the montmorillonite clay is an acidic calcium montmorillonite clay having, prior to treatment with the phosphorous-containing acid, a moisture content ranging up to about 20 wt. %, a residual acidity in the range of about 3 to about 30 mg KOH/g, and a surface area of about 300 $M^2/g$ or greater.

23. The process of claim 18, wherein the olefin contains from 14 to 16 carbon atoms.

24. The process of claim 18, wherein the phosphorous-containing acid is hypophosphorous acid, hypophosphoric acid, orthophosphoric acid, metaphosphoric acid, or polyphosphoric acid.

25. The process of claim 18, wherein the phosphorous-containing acid is orthophosphoric acid.

* * * * *